United States Patent [19]

Maale

[11] Patent Number: 4,653,487
[45] Date of Patent: Mar. 31, 1987

[54] INTRAMEDULLARY ROD ASSEMBLY FOR CEMENT INJECTION SYSTEM

[76] Inventor: Gerhard E. Maale, Texas Tech University Health Sciences Center, Lubbock, Tex. 79430

[21] Appl. No.: 823,658

[22] Filed: Jan. 29, 1986

[51] Int. Cl.$^4$ ............................................. A61F 5/04
[52] U.S. Cl. ........................... 128/92 VQ; 128/92 YZ; 128/92 VP
[58] Field of Search ........ 128/92 XO, 92 XP, 92 YZ, 128/92X, 92 YF

[56] References Cited

U.S. PATENT DOCUMENTS

| | | | |
|---|---|---|---|
| 3,223,083 | 12/1965 | Cobey | 128/92 XO |
| 4,277,184 | 7/1981 | Solomon | 128/92 XO |
| 4,338,925 | 7/1982 | Miller | 128/92 XO |
| 4,399,814 | 8/1983 | Pratt, Jr. et al. | 128/92 XD |
| 4,462,394 | 7/1984 | Jacobs | 128/92 XO |
| 4,494,535 | 1/1985 | Haig | 128/92 XP |
| 4,546,767 | 10/1985 | Smith | 128/92 XO |
| 4,576,152 | 3/1986 | Müller et al. | 128/92 XO |

Primary Examiner—Gene Mancene
Assistant Examiner—C. W. Shedd
Attorney, Agent, or Firm—Mason, Fenwick & Lawrence

[57] ABSTRACT

Apparatus and methods for intramedullary fixation of abnormal bone, such as a femur, wherein an axially elongated intramedullary rod is provided having outwardly projecting thin fins or elongated sharp edge formations at circumferentially spaced locations spanning substantially the length of the rod to provide rotational stability, and provided with a plurality of holes in each of the surface portions between pairs of the fins or edge formations, which are normally closed by screw plugs or plugged with methylmethacrelate plugs, but which may be removed selectively prior to rod insertion into the medullary canal to permit discharge of methylmethacrelate cement or the like into desired surrounding bone areas. A coupling formation such as a threaded coupling neck is provided at one end of the rod, to be assembled with a tube extending from a piston aided dispensing device similar to a caulking gun to force the low viscosity cement into the hollow interior bore of the rod and discharge through apertures where the plugs have been removed or holes are open in the rod.

23 Claims, 12 Drawing Figures

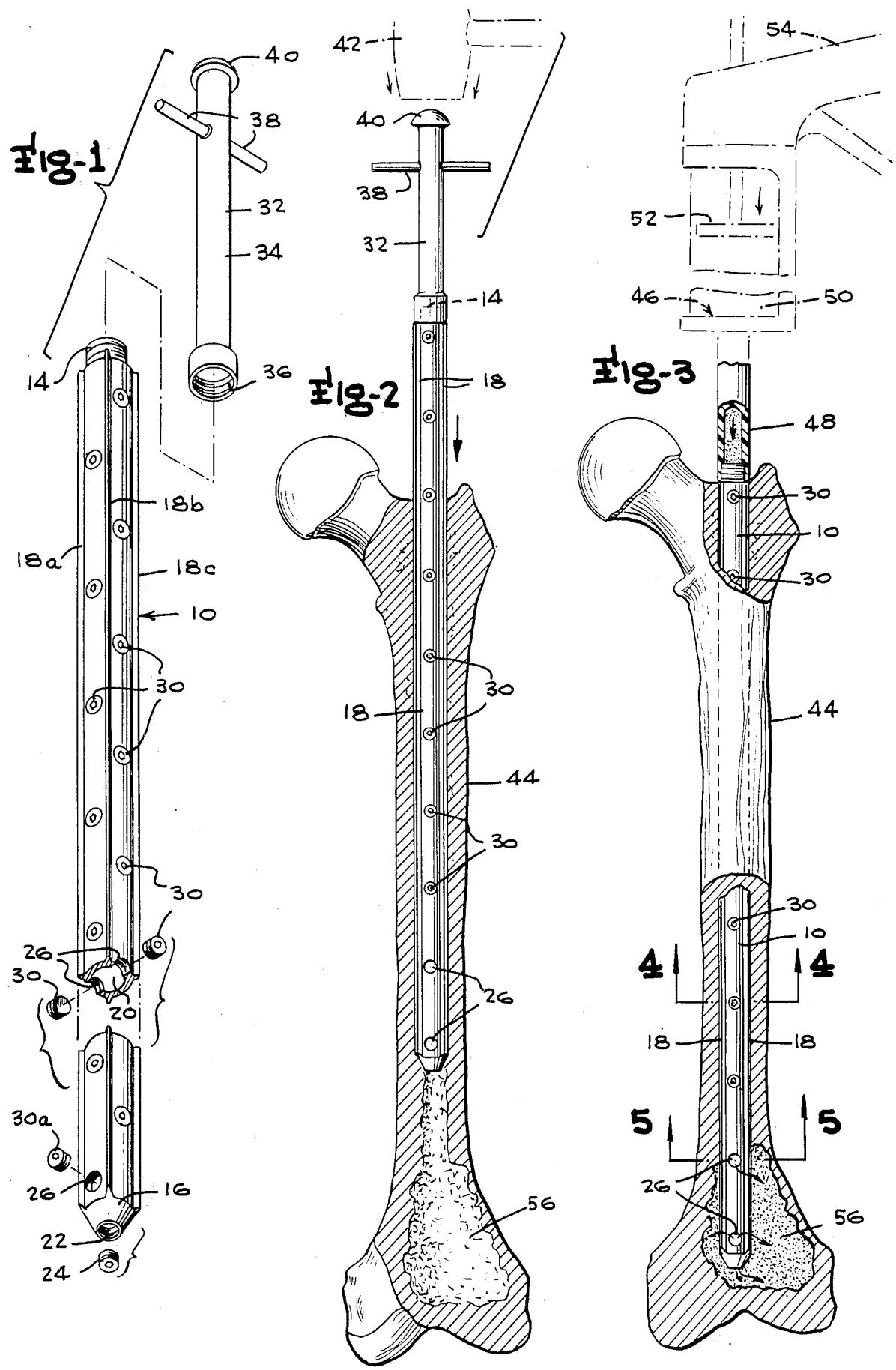

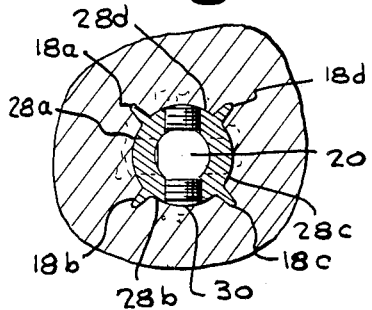
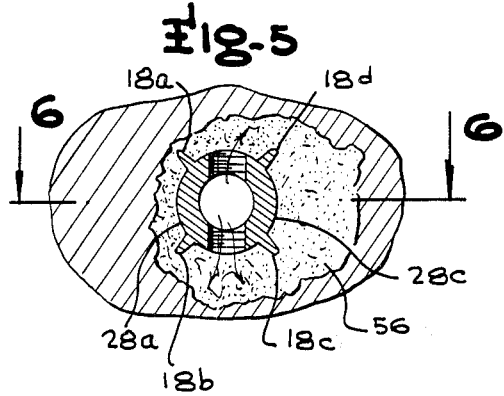
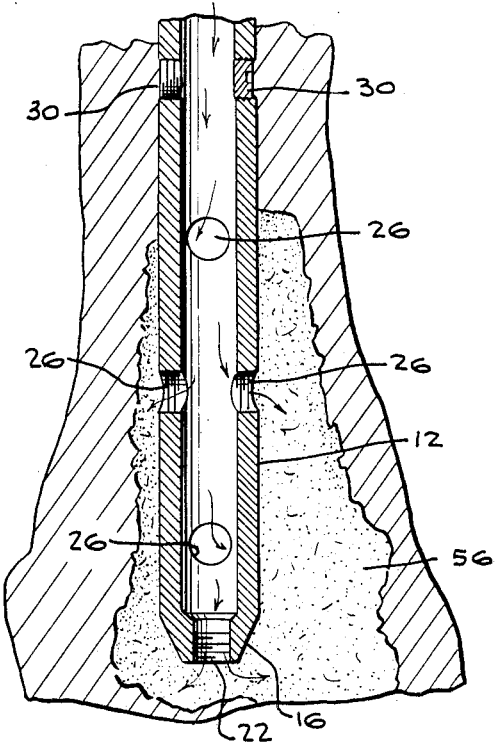
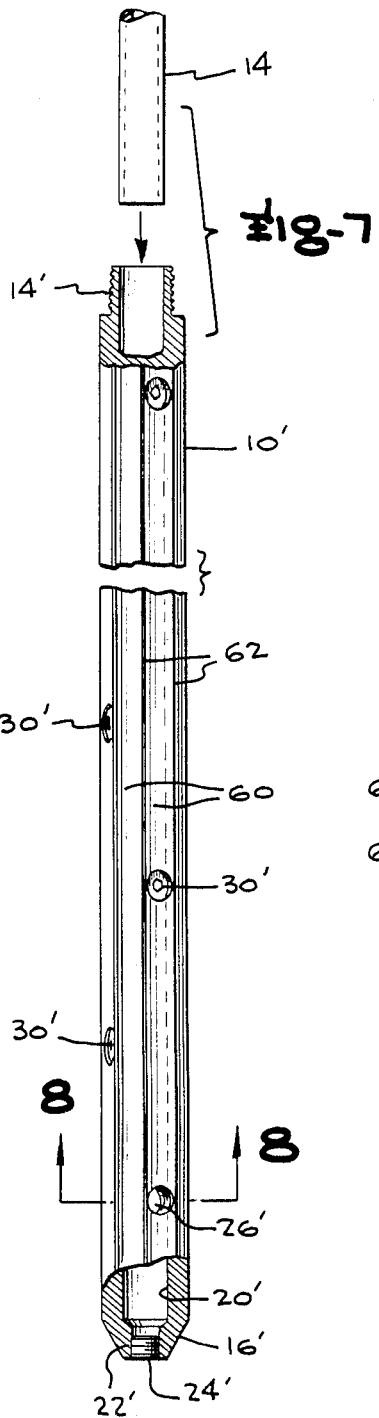
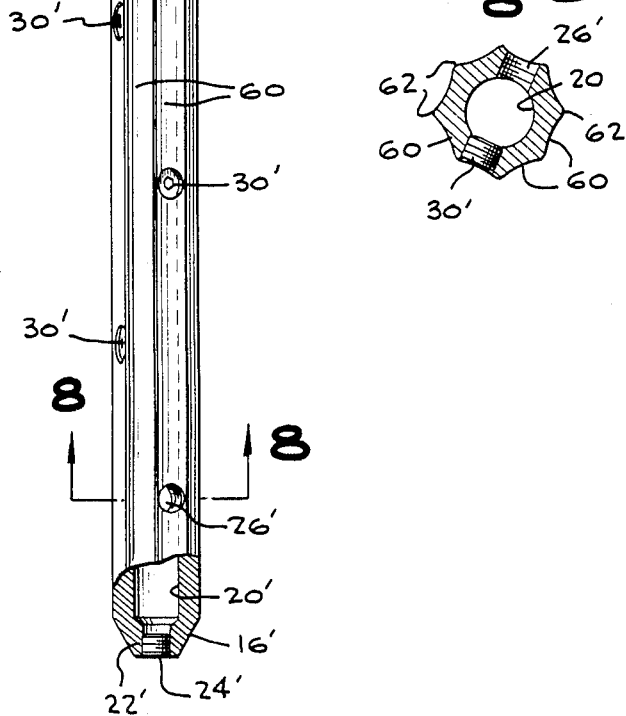

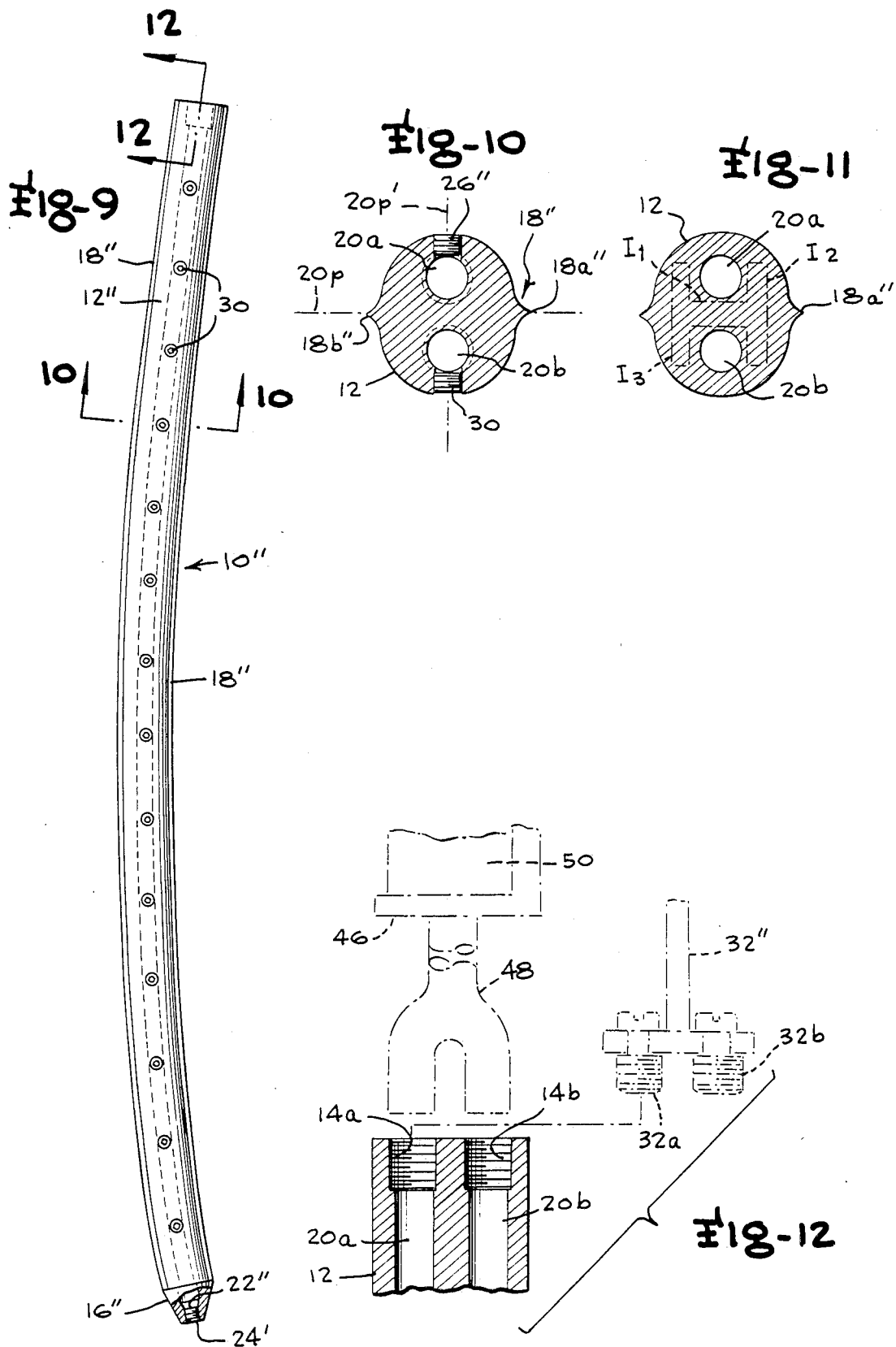

INTRAMEDULLARY ROD ASSEMBLY FOR CEMENT INJECTION SYSTEM

BACKGROUND AND OBJECTS OF THE INVENTION

The present invention relates in general to apparatus and methods for intramedullary fixation of abnormal bone, particularly applicable to femurs, tibia and humerus, and more particularly to intramedullary rods for fixation of impending pathological fracture, allograft fixation, or augmentation of osteopenic skeleton, incorporating means for feeding cement through the intramedullary rod to exit from the rod into surrounding bone tissue at variable locations.

Heretofore, various types of intramedullary rods have been provided for fixation of bones, such as for fixation of the femur and similar bones of appendages of the human body, particularly for fracture fixation. For example, Burstein patent Nos. 3,977,398 and 3,783,860 disclose intramedullary rods for use in fracture fixation, which in the later patent involves a rod which has longitudinal flutes but is closed at both ends, and in the earlier patent is in the form of a hollow tube having flutes and having castellated ends to provide sharp cutting surfaces and angled face guide projections.

The Branemark patent No. 4,065,817 discloses an arrangement wherein a perforated or slotted tube is inserted into a hole drilled in the bone and then the stem of a prosthesis is inserted in the hollow bore of the tube and cement is inserted to set the prosthesis in the tube, and cement is forced through openings into contact with the bone to secure the tube in place for a short term or mid term period.

The present invention is designed primarily for treatment of impending pathological fractures of bones from metastatic cancer, although it also is applicable to allograft fixation and augmentation of osteopenic skeleton.

The apparatus of the present invention has its therapeutic application for patients who are suffering from metastatic cancer to bone. For these patients, the interest is not directed at curing the cancer, but it is more directed at palliation from pathological fractures caused by the cancer. These fractures are both painful and cause loss of structural stability provided by the bones. The apparatus of the present invention is to provide for a quick and efficient means of dealing with these tumors in the bone.

An object of the present invention is the provision of an intramedullary rod and cement injection system for the treatment of abnormal bones, such as treatment of impending pathological fractures, allograft fixation, augmentation of osteopenic skeleton, and the like, including a novel configuration and structural assembly for a hollow intramedullary rod having selectively removable screw threaded plugs or open holes in a series of selectable discharge openings along the axial height of the rod for discharge of cement such as methylmethacrelate to surround the rod in adjacent bone tissue. A piston aided dispensing device similar to a caulking gun is coupled to the rod after insertion of the rod into the medullary and activated to force the low viscosity cement into the hollow interior bore of the rod for discharge through appatures where the plugs have been removed or holes are open. By augmenting the intramedullary rod with methylmethacrelate cement injected into the rod allowing it to surround the rod, this will provide for better fixation in areas which are involved with cancer, increasing the structural support of the involved bone, thermal kill of cancer, and an increasing of the structural strength of the intramedullary rod. The methylmethacrelate cement which exits around the rod at the desired level will fill defects caused by tumor or provide additional strength to the rod when it is used for osteoprotic bone or the fixation of allografts.

Another object of the present invention is the provision of a system as described in the immediately preceding paragraph, wherein the intramedullary rod is provided with a plurality of radially outwardly projecting thin fins spanning the vertical height of the rod to provide rotational stability, and wherein the rod is provided with a plurality of holes spaced vertically in each of the surface portions between pairs of the fins, normally closed by screw plugs or plugged with methylmethacrelate plugs, but which may be removed selectively prior to rod insertion to permit discharge of the cement into the desired surrounding bone area.

Yet another object of the present invention is the provision of a system as described in the two immediately preceding paragraphs, wherein the rod is a vertically elongated hollow tube and may be employed with externally threaded cylindrical plugs or hollow holes, positioned within the rod in selected corrolation with injection of cement to produce exit of cement into surrounding bone tissue at plural vertically spaced locations when required.

Another object of the present invention is the provision of a system as described in the immediately preceding paragraphs, wherein the rod is a vertically elongated hollow tube having a cross-sectional configuration of the rod such as to provide a pair of substantially parallel interior channels or tubes extending alongside each other along similar paths spaced diametrically opposite the center of the rod such that the remainder of the rod forms an I-beam type construction, with the holes spaced longitudinally along the channels or tubes which are normally closed by screw plugs and open in diametrically opposite directions from the channels.

Other objects, advantages and capabilities of the present invention will become apparent from the following detailed description, taken in conjunction with the accompanying drawings illustrating a preferred embodiment of the invention.

BRIEF DESCRIPTION OF THE FIGURES

FIG. 1 is an exploded perspective view of an intramedullary rod and associated rod insertion device embodying the present invention for carrying out the herein described method of rod insertion and cement injection;

FIG. 2 is a side elevation view showing the intramedullary rod and a rod insertion device assembled and in process of insertion into a femur, with parts of the femur broken away to illustrate the rod inserted therein;

FIG. 3 is a side elevation view showing the intramedullary rod fully inserted in the femur, the femur being shown with parts broken away, and with the cement discharge gun attached thereto indicated in phantom lines;

FIGS. 4 and 5 are horizontal transverse section views taken along the lines 4—4 and 5—5 of FIG. 3;

FIG. 6 is a fragmentary section view to enlarged scale showing the lower portion of the intramedullary rod and adjacent bone structure, taken along the line 6—6 of FIG. 5;

FIG. 7 is a side elevation view of an intramedullary rod and associated filler tube, for a rod of a slightly modified configuration;

FIG. 8 is a horizontal transverse section view taken along the line 8—8 of FIG. 7;

FIG. 9 is a side elevation view of another modified form of the intramedullary rod of the present invention, of still another configuration;

FIG. 10 is a horizontal transverse section view thereof taken along line 10—10 of FIG. 9;

FIG. 11 is a somewhat diagrammatic transverse section view similar to FIG. 10, but showing in broken lines the I-beam type configuration produced; and, FIG. 12 is a fragmentary vertical section view of the upper end portion of the rod of FIG. 9, taken along the line 12—12 of FIG. 10.

DETAILED DESCRIPTION OF PREFERRED EMBODIMENTS

Referring to the drawings wherein like reference characters designate corresponding parts throughout the several figures, the cement injection intramedullary fixation rod of the present invention is indicated generally by the reference character 10 and comprises a rigid elongated hollow rod of materials such as medical grade cobalt chromium alloy or stainless steel, or possibly vitallium, which is basically formed as an elongated generally cylindrical rigid rod member 12 having an externally threaded coupling formation 14 at its upper end, and in the illustrated embodiment, has a convergently tapering or conical lower end or leading end 16. The rod member 12 has a plurality of elongated narrow fins 18 spanning the major portion of the axial length of the cylindrical rod member 12 and located, in the illustrated embodiment, at quadrature or 90° circumferentially spaced locations. In the illustrated embodiment, the fins 18, four of which are shown and are designated 18a-18d, project 1 mm from the cylindrical surface of the rod body portion 12 and the rod body 12 is hollow providing a cylindrical bore 20 extending the length thereof to convergently tapering lower or leading end 16 providing a tubular body of approximately 2 mm wall thickness. The lower or leading end 16 of the intramedullary rod is also provided with an internally threaded opening 22 communicating with the bore 20, which is normally closed by an externally threaded cylindrical metal plug 24 having a hexagonal socket opening through the lower or exposed face thereof adapted to receive an Allen type wrench or similar tool for threading the plug 24 into and out of the opening 22 as desired.

Also, along the axial length of the cylindrical body portion 12 of the intramedullary rod 10 are a plurality of internally threaded or non threaded lateral discharge openings 26, located in the face portions of the cylindrical rod body portion 12 between each successive pair of fins 18, for example between fins 18a and 18b, and between fins 18b and 18c, etc., located for example 1 inch apart vertically in each quadrature segment of the body portion 12 between a pair of fins 18 with the lateral discharge holes 26 located in a diametrically opposite pair of rod segments, for example segments 28b and 28d staggered ½ inch axially relative to the lateral discharge holes 26 in the other diametric pair of rod body portion segments 28a, 28c. The lateral discharge holes or openings 26 in the tubular body portion 12 of the intramedullary rod are normally closed by removable externally threaded cylindrical metal plugs 30, threaddedly coupled in the internally threaded openings 26, and having hexagonal sockets, for example as indicated at 30a similar to the hexagonal socket in the plug 24, to receive an Allen wrench or similar tool for threading the plug into and out of its companion opening 26. The holes 26 may be selectively closed by methylmethacrelate cement to plug the holes.

An insertion bar device, as indicated at 32 in FIGS. 1 and 2 is provided in the illustrated embodiment, which is in the form of an elongated steel bar portion 34 of cylindrical configuration having an enlarged downwardly opening, internally threaded socket formation 36 in its lower end to be threaded onto the threaded coupling portion 14 at the upper or approximal end of the intramedullary rod 10. The rod insertion device 32 includes a pair of transverse rod-like extensions or cross-arms 38 near its upper end for directional control, and an anvil head 40 at the end opposite the coupling formation 36 to be impacted with a hammer, indicated at 42 in phantom lines in FIG. 2, to facilitate driving of the intramedually rod 10 into the canal of the femur or similar bone, after drilling of an appropriately sized bore or other convention formation of such a receptor bore along the intramedullary canal portion of the bone, such as the femur 44 as indicated in the drawings, to be treated.

The system of the present invention also involves the provision of a cement injector gun, for example as indicated at 46, having an elongated hollow tubular discharge or filler tube, for example of strong plastic or the like, as indicated at 48 threaded at its discharge end to be threaddedly coupled onto the coupling formation 14 of the intramedullary rod after it has been inserted into the femur or other receptor bone, and connected to a charge receiving barrel or chamber, indicated at 50, having an associated piston discharge assistant 52 and activator mechanism with trigger and handle 54, similar to a normal caulking gun, to receive a charge of the methylmethacrelate cement of low viscosity and discharge it through the tube 48 into the interior bore 20 of the intramedullary rod. A separate injection system may be used where the elongated filler tube is inserted in the hollow internal diameter of the rod at 14 and low viscosity cement is injected through the cement gun mechanism 46 at the desired level of the opened hole, so selected pressurization can occur at the exit holes. In such a case a long filler tube 14 inserted into the bore 20 to the desired level permits selection of the holes through which cement is discharged.

In the use of the hereinabove described intramedullary rod and cement injection system, the intramedullary canal of the receptor bone, for example the femur 44, which may have, in the described example, a metastatic cancer tumor zone 56, is prepared in conventional manner for reception of the intramedullary rod, and the intramedullary rod is assembled to the rod insertion bar device 32 and driven, as by a hammer 42, axially downwardly into the canal of the femur, shown in process of insertion in FIG. 2 and as completely inserted in FIG. 3. Prior to insertion of the intramedullary rod 10, after examination of the bone to determine the location or level of the metastatic cancer tumor area or other area to be loaded with the methylmethacrelate cement, the threaded plugs 30 for the lateral discharge openings 26 of the intramedullary rod at the appropriate locations, for example the two lower sets of lateral discharge openings in the example illustrated in FIGS. 2 and 3, are removed leaving the openings 26 at these locations free for discharge of methylmethacrelate cement into the surrounding bone tissue. The discharge tube portion 48 of the cement injector gun assembly 46 is then coupled onto the threaded coupling 14 of the intramedullary rod after removal of the rod insertion device 32, and the methylmethacrelate cement is forced by activation of the piston 52 to discharge through the tube 48 and the bore 20 of the intramedullary rod and cause lateral discharge or exit of cement from the open passages or unplugged openings 26 in the lower end portion of the metramedullary rod to, for example, infuse the cement into the bone area surrounding the rod, providing for better fixation in areas which are involved with cancer, increasing the structural support of the involved bone, effecting thermal kill of cancer, and increasing the structural strength of the intramedullary rod. The methylmethacrelate cement thus plugs the defects in the femur and achieves rigid fixing of the rod in the bone.

The intramedullary rod structure of the present invention also lends itself to other procedures which may be followed to select particular levels or axial zones of the intramedullary rod from which the cement is to be discharged into surrounding bone tissue, for example employing a solid plastic cylindrical rod plug having a diameter corresponding to the diameter of the bore 20 and of various axial lengths. For example, if the tumor area is located in the intermediate zone generally midway between the top and bottom of the femur, the amount of methylmethacrelate cement required to be injected into the rod 10 may be reduced by introducing the plastic cylindrical plug into the bore 20 after driving the rod 10 to the appropriate position in the bone, with the rod plug for example spanning the axial length of the lower two sets or lower three sets of discharge openings 26, and the cement can then be forced into the upper end of the bore 20 of the intramedullary rod 10 and discharged into tumor area along the vertical mid region of the femur, assuming the threaded screw plugs 30 to have been removed from the lateral discharge holes 26 in such mid region, discharging the cement into the tumor area to fill the tumor area in the axial mid region of the bone. Similarly, if tumor areas or fixation areas near the upper and lower ends of the intramedullary rod are to be provided without discharge of cement in the mid region, the lowermost discharge openings 25 may be opened by removal of their threaded screw plugs 30, the methylmethacrelate cement is then forced into the bore of the intramedullary rod 10 by the cement discharge gun 46 to inject the cement into the tumor area or surrounding tissue at the lower end portion of the rod, a cylindrical plastic plug of the diameter of the bore 20 of the rod having an axial length spanning the desired axial zone may then be inserted to occupy the mid region of the rod 10, and, with the threaded screw plugs 30 in the uppermost sets of holes 26 removed, the cement gun 46 can again be attached and insert cement under pressure to force it to discharge outwardly into surrounding bone tissue through the open upper sets of discharge openings 26 to also inject the cement into the bone tissue in the upper femur region at the desired location.

FIGS. 7 and 8 illustrate a modified form which the intramedullary rod 10 can take, here indicated by reference character 10', having the threaded upper coupling end portion 14' and the tapered lower or leading end portion 16' similar to the previously described embodiment, and having other components indicated by reference characters which are the primes of the reference characters used in describing the earlier embodiment. In this embodiment, however, rather than employing thin rectalinear rib-like fins projecting radially outwardly from the surface of the cylindrical tubular body portion of the intramedullary rod, the exterior surface of the rod is formed with parallel concave flutes 60 which provide rib-like pointed edge formations 62 at the junctures of adjoining flutes 60 spanning the vertical height of the intramedullary rod and serving functions similar to the rib-like fins 18 of the first embodiment securing the intramedullary rod against rotation.

FIGS. 9 to 12 illustrate a further modified form which the intramedullary rod 10 can take, herein indicated by reference character 10", having a different transverse cross sectional shape providing two hollow bores or cavities, here indicated as 20a and 20b extending the length thereof along one diametric cross sectional axis of the rod and having a pair of rectalinear rib like fins projecting outwardly from the surface of the tubular body portion of the rod along a diametric axis which is perpendicular to the diametric axis through the centers of the two bores or cavities 20a, 20b. The intramedullary rod 10", as illustrated in FIG. 9, is not precisely rectalinear in this illustration, and in fact may not be precisely rectalinear in the earlier described embodiments, since, it will be appreciated by those ordinarily skilled in the art, the rod is shaped longitudinally so as to correspond to the configuration of the typical bones, such as femurs, into which it is to be inserted. As in the earlier described embodiments, the intramedullary rod 10" has a convertently tapering or conical lower or leading end, indicated at 16", and is provided in this embodiment with a pair of elongated narrow fins 18" extending the major portion of the axial length of this cylindrical rod member 12 and located in outwardly projecting diametrically opposite positions along an imaginary curving plane 20p formed by the corresponding diametric axes of the rod along the longitudinal extent thereof, which plane 20p is disposed perpendicular to or at a 90° angle relative to the imaginary curving plane 20p' extending through the centers of the two paired bores or channels 20a, 20b. The intramedullary rod 10" of this embodiment is preferably formed of a metal alloy appropriate for insertion and residence in the host bone, and in one satisfactory embodiment, the distance between the tips of the fin formations is 11 mm, with the bores or injection tubes 20a, 20b having a diameter of about 2.5 mm.

As in the previously described embodiment, the lower or leading end 16" of the rod 10" is provided with an internally threaded opening 22" communicating with the bores, which is normally closed by an externally threaded cylindrical metal plug 24", and, along the axial length of the body portion 12", a plurality of internally threaded lateral discharge openings 26" are provided, located in the face portions of the rod body portion 12", with their centers located in the curving diametric plane 20p' extending through the centers of the bores or channels 20a, 20b. These may be located, for example, one inch apart vertically and be disposed substantially mid way between the tips of the fins 18a" and 18b". The discharge holes or openings 26" are normally closed by removable externally threaded cylindrical metal plugs 30", threadedly coupled in the internally threaded openings 26", and having hexagonal sockets, as in the previously described embodiment, or other non-round cavities therein to receive an Allen wrench or similar tool for threading the plug into and out of its companion opening.

It will be appreciated from inspection of FIG. 11 that the cross-sectional configuration resulting from this particular construction having the pair of longitudinally extending injection bores or channels 20a, 20b resembles somewhat the configuration of an I-beam, here indicated diagrammatically in heavy broken lines by the reference character I, having the web portion I-1 formed by the portion of the rod lying between the two diametrically oppositely spaced bores or channels 20a, 20b and extending along the diametric plane of the fins 18a'' and 18b'', as well as a pair of flange portions I-2 and I-3 joined to the ends of the web portion I-1. This provides increased strength in the resultant fixation system because of this I-beam type rod configuration. Since two longitudinally extending injection channels or bores 20a, 20b are provided in this embodiment, obviously the coupling formation at the upper end of the rod in this embodiment must have two threaded coupling formations 14a and 14b at the upper ends of the bores or channels 20a, 20b, similar to the externally threaded coupling formation 14 of the previously described embodiments, but in this case being internally threaded as shown in FIGS. 9–12, to be coupled to an insertion device 32'', similar to the insertion device 32, but having two externally threaded coupling screws 32a, 32b journaled in the lower end portion of the insertion device 32'', having Allen wrench sockets or similar formations in their upper ends, to be threaded into the internally threaded coupling formations 14a, 14b. Also, the cement injector gun for use with this embodiment, which would be similar to the cement injector gun 46 of the previously described embodiment, would be provided with a tubular discharge or filler tube which at its lower end has a pair of exit openings sized to fit into the internally threaded coupling socket formations 14a, 14b at the upper end of the rod 10'' for piston assisted discharge of the methylmethacrelate cement into the bores 20a, 20b of the rod in the manner described in connection with the previously described embodiments.

It will be apparent that other specific configurations may be employed for the intramedullary rod providing the novel features and concepts of the embodiments herein described, and it is desired therefor that the scope of the invention be understood to embrace modifications which fall within the scope of the appended claims.

I claim:

1. An intramedullary rod assembly for fixation of abnormal bone such as fixation of impending pathological fracture as in bone areas involved with cancer, allografts fixation, augmentation of osteogenic skeleton, and the like, comprising an elongated hollow tubular rod member of medical grade metal of generally cylindrical form having an internal bore extending the length thereof from a distal end to a proximal end surrounded along its length by an outer wall, a threaded first coupling formation at the proximal end of the rod member to be coupled to a threaded coactive coupling formation of an insertion bar device for inserting the rod member into a recipient medullary canal and subsequently to a discharge tube of a cement injector gun device for injecting methylmethacrelate cement or the like into the bore of the rod member, the rod member having a plurality of sharp exterior protruding longitudinal edge formations along circumferentially spaced radial planes of the rod member spanning substantially the length thereof to extend into bone tissue and provide rotational stability for the rod, said outer wall having a plurality of axially and circumferentially spaced threaded apertures in the portions thereof intervening between said edge formations and threaded plug members removably mounted in said apertures for selective removal before inserting the rod member in recipient bone to leave certain of said apertures open for discharge of the cement into adjacent bone portions when the rod is fully implanted and the cement is injected into the bone of the rod member.

2. An intramedullary rod assembly as defined in claim 1, wherein said threaded plug members are substantially cylindrical disc shaped plugs having a threaded periphery to be threadedly coupled into said apertures in the rod member outer wall and having a flat outer face to be located substantially flush with the adjoining outer surface portions of the outer wall portions intervening between said edge formations.

3. An intramedullary rod assembly as defined in claim 2, wherein said axially and circumferentially spaced threaded apertures in the outer wall of said rod member are arranged in a first set of diametrically opposite pairs of such apertures and one diametrically opposite pair of intervening outer wall portions between a respective pair of said edge formations and spaced substantially equidistant from each other axially of the rod member along the length of the rod and a second set of threaded apertures spaced axially similar distances from each other in another pair of diametrically opposite intervening outer wall portions between adjacent respective pairs of said edge formations with the second set of apertures being located in staggered positions relative to the apertures of said first set.

4. An intramedullary rod assembly as defined in claim 2, wherein said proximal end of said rod member serves as the leading end thereof upon insertion of the rod member into the recipient bone, and is of convergently tapering configuration having a threaded aperture there through communicating with said bore and a threaded plug member removably mounted therein for selective removal before insertion of the rod member.

5. An intramedullary rod assembly as defined in claim 2, wherein the exterior surface of said rod member is a cylindrical surface over substantially the axial length thereof interrupted by said edge formations, and said edge formations are provided with radially outwardly projecting thin fins extending the axial length of the rod member along said circumferentially spaced radial planes.

6. An intramedullary rod assembly as defined in claim 2, wherein the exterior surface of said rod member is fluted to provide a plurality of circumferentially spaced concave flutes extending between respective circumferentially spaced pairs of said edge formations and spanning substantially the axial length of the rod member, said threaded apertures being located in centered relation within said concave flutes and having a diameter to span the major portion of the transverse distance between the adjacent pairs of edge formations.

7. An intramedullary rod assembly as defined in claim 1, wherein said axially and circumferentially spaced threaded apertures in the outer wall of said rod member are arranged in a first set of diametrically opposite pairs of such apertures and one diametrically opposite pair of intervening outer wall portions between a respective pair of said edge formations and spaced substantially equidistant from each other axially of the rod member along the length of the rod and a second set of threaded apertures spaced axially similar distances from each other in another pair of diametrically opposite intervening outer wall portions between adjacent respective pairs of said edge formations with the second set of apertures being located in staggered positions relative to the apertures of said first set.

8. An intramedullary rod assembly as defined in claim 7, wherein said proximal end of said rod member serves as the leading end thereof upon insertion of the rod member into the recipient bone, and is of convergently tapering configuration having a threaded aperture there through communicating with said bore and a threaded plug member removably mounted therein for selective removal before insertion of the rod member.

9. An intramedullary rod assembly as defined in claim 8, wherein the exterior surface of said rod member is a cylindrical surface over substantially the axial length thereof interrupted by said edge formations, and said edge formations are provided with radially outwardly projecting thin fins extending the axial length of the rod member along said circumferentially spaced radial planes.

10. An intramedullary rod assembly as defined in claim 8, wherein the exterior surface of said rod member is fluted to provide a plurality of circumferentially spaced concave flutes extending between respective circumferentially spaced pairs of said edge formations and spanning substantially the axial length of the rod member, said threaded apertures being located in centered relation within said concave flutes and having a diameter to span the major portion of the transverse distance between the adjacent pairs of edge formations.

11. An intramedullary rod assembly as defined in claim 7, wherein the exterior surface of said rod member is a cylindrical surface over substantially the axial length thereof interrupted by said edge formations, and said edge formations are provided with radially outwardly projecting thin fins extending the axial length of the rod member along said circumferentially spaced radial planes.

12. An intramedullary rod assembly as defined in claim 7, wherein the exterior surface of said rod member is fluted to provide a plurality of circumferentially spaced concave flutes extending between respective circumferentially spaced pairs of said edge formations and spanning substantially the axial length of the rod member, said threaded apertures being located in centered relation within said concave flutes and having a diameter to span the major portion of the transverse distance between the adjacent pairs of edge formations.

13. An intramedullary rod assembly as defined in claim 1, wherein said proximal end of said rod member serves as the leading end thereof upon insertion of the rod member into the recipient bone, and is of convergently tapering configuration having a threaded aperture there through communicating with said bore and a threaded plug member removably mounted therein for selective removal before insertion of the rod member.

14. An intramedullary rod assembly as defined in claim 13, wherein the exterior surface of said rod member is a cylindrical surface over substantially the axial length thereof interrupted by said edge formations, and said edge formations are provided with radially outwardly projecting thin fins extending the axial length of the rod member along said circumferentially spaced radial planes.

15. An intramedullary rod assembly as defined in claim 1, wherein the exterior surface of said rod member is a cylindrical surface over substantially the axial length thereof interrupted by said edge formations, and said edge formations are provided with radially outwardly projecting thin fins extending the axial length of the rod member along said circumferentially spaced radial planes.

16. An intramedullary rod assembly as defined in claim 1, wherein the exterior surface of said rod member is fluted to provide a plurality of circumferentially spaced concave flutes extending between respective circumferentially spaced pairs of said edge formations and spanning substantially the axial length of the rod member, said threaded apertures being located in centered relation within said concave flutes and having a diameter to span the major portion of the transverse distance between the adjacent pairs of edge formations.

17. An intermedullary rod assembly as defined in claim 1, wherein said bore constitutes a first tubular channel for the cement located to one side of a center longitudinal axis of the rod member between such axis and exterior face portions of said outer wall of the rod member, said rod member including a second bore like the first-mentioned bore forming a second tubular channel coextensive longitudinally with said first channel and having a center axis spaced uniformly from the center axis of the first channel substantially equidistant from and diametrically opposite said longitudinal axis as the center axis of said first channel, the remaining portions of said rod member cross-sectionally resembling an I-beam configuration with the web of the I-beam configuration located in diametric axis perpendicular to the diametric axis through the center axis of said channels.

18. An intramedullary rod assembly as defined in claim 17, wherein said apertures are provided in axially spaced relation along the longitudinal extent of each of said channels opening from the associated channel through the exterior face of the outer wall of said rod member.

19. An intramedullary rod assembly as defined in claim 18, wherein said sharp protruding edge formations form a single pair of radically outwardly projecting thin fins extending the axial length of the rod member and located in the plane defined by the diametric axis containing the web of said I-beam configuration.

20. An intramedullary rod assembly as defined in claim 17, wherein said apertures are provided in axially spaced relation along the longitudinal extent of each of said channels opening from the associated channel through the exterior face of the outer wall of said rod member and located substantially midway between a pair of said sharp protruding longitudinal edge formations.

21. An intramedullary rod assembly as defined in claim 20, wherein said sharp protruding edge formations form a single pair of radically outwardly projecting thin fins extending the axial length of the rod member and located in the plane defined by the diametric axis containing the web of said I-beam configuration.

22. An intramedullary rod assembly as defined in claim 17, wherein said sharp protruding edge formations form a single pair of radically outwardly projecting thin fins extending the axial length of the rod member and located in the plane defined by the diametric axis containing the web of said I-beam configuration.

23. A method for intramedullary rod fixation of abnormal bone such as fixation of impending pathological fracture as in bone areas involved with cancer, allograft fixation, augmentation of osteopenic skeleton, and the like, comprising the steps of forming an elongated insertion hole in a recipient medullary canal or the like of recipient bone, inserting an intramedullary rod therein having an elongated hollow tubular rod portion of medical grade metal of generally cylindrical form including an internal bore extending the length thereof from a distal end to a proximal end surrounded by an outer wall and having a threaded coupling formation at the proximal end of the rod member, the intramedullary rod also having a plurality of sharp exterior protruding rectalinear edge formations along circumferentially spaced radial planes of the like extending substantially the length thereof and having axially and circumferentially spaced threaded apertures in the intervening portions thereof between said rod formations normally closed by removable threaded plug members, removing plug members from selected ones of said threaded apertures prior to insertion of the rod member to leave open apertures at locations where it is desired to have methylmethacrelate cement or the like discharge from the bore of the rod member into adjacent bone tissue, coupling a cement injector gun device having a charge of cement and discharge assisted piston means to the coupling formation of the rod member, activating the discharge assisted piston means to force the methylmethcrelate cement or the like into the bore of the rod member for discharge outwardly thereof through the threaded apertures left open by removal of their associated plugs, and decoupling the cement injector gun device from the intramedullary rod.

* * * * *